United States Patent [19]

Iwasaki et al.

[11] Patent Number: 5,639,789
[45] Date of Patent: Jun. 17, 1997

[54] BUTADIENE DERIVATIVES AND PROCESS FOR USING THE SAME

[75] Inventors: Tameo Iwasaki, Nishinomiya; Takashi Nishitani, Toyonaka; Akio Ohtani, Kawaguchi; Masanori Inamasu, Misato, all of Japan

[73] Assignee: Tanabe Seiyaku Co., Ltd., Osaka, Japan

[21] Appl. No.: 436,564

[22] Filed: May 8, 1995

Related U.S. Application Data

[62] Division of Ser. No. 33,804, Mar. 18, 1993, Pat. No. 5,514,815.

[30] Foreign Application Priority Data

Mar. 26, 1992 [JP] Japan ................. 4-119480
Mar. 26, 1992 [JP] Japan ................. 4-119481
Mar. 26, 1992 [JP] Japan ................. 4-119482
Mar. 26, 1992 [JP] Japan ................. 4-119483

[51] Int. Cl.$^6$ ................. C07D 401/06; A61K 31/44
[52] U.S. Cl. ................. 514/539; 514/237.8; 514/354; 514/355; 514/357; 544/162; 546/316; 546/323; 546/335; 560/39; 560/41
[58] Field of Search ................. 560/39, 41; 546/316, 546/323, 335; 544/162; 514/355, 354, 357, 237.8, 539

[56] References Cited

U.S. PATENT DOCUMENTS 4,145,536  3/1979  Heller .
4,182,629  1/1980  Heller .

FOREIGN PATENT DOCUMENTS 0070631  1/1983  European Pat. Off. .
0420397  4/1991  European Pat. Off. .
2441759  3/1975  Germany .

OTHER PUBLICATIONS

Journal of Chemical Society Perkin Transactions 1, vol. 22, pp. 2227–2232 (1975).
Nouveau Journal de Chimie, vol. 1, No. 5, pp. 413–418 (1977).
Chemical Abstracts, vol. 85, 45931a. (1964).
Chemical Abstracts, vol. 114, 80786w. (1993).
Patent Abstracts of Japan, JP-A-1250351 (Oct. 1989).

Chemical Abstracts, vol. 110, No. 23, 2112466w (Jun. 1989).
Artherosclerisos, vol. 95, pp. 105–117 (1992).
JAMA, vol. 250, pp. 2743–2744 (1983).
Circulation, vol. 71, pp. 627–631 (1985).
JAMA, vol. 255, pp. 237–239 (1986).
Circulation, vol. 85, No. 1, pp. 305–312 (1992).
B. Widman et al., Clinica Chimica Acta, 127, pp. 279–288, 1983.
J. Chmielewska et al., Thrombosis Research, 31; pp. 427–436, 1983.
S. Dawson et al., Artherosclerosis, 95, pp. 105–117, 1992.
JAMA, vol. 250, No. 20, pp. 2743–2744, 1993.
K. Rentrop, Circulation, vol. 71, No. 4, pp. 627–631, 1985.
JAMA, vol. 255, No. 2, pp. 237–239, 1986.
M. Levi et al., Circulation, vol. 85, No. 1, pp. 305–312, 1992.

Primary Examiner—Jacqueline Haley
Attorney, Agent, or Firm—Birch, Stewart, Kolasch & Birch, LLP

[57] ABSTRACT

Novel butadiene derivatives of the formula [I]:

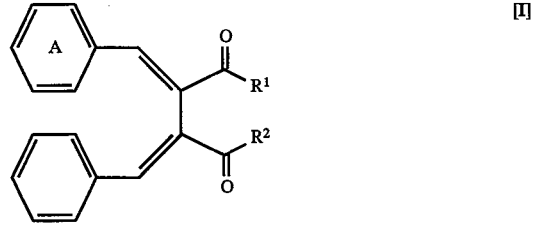

wherein Ring A is tri-lower alkoxyphenyl, $R^1$ and $R^2$ combine each other to form a group of the formula:

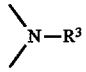

or one of $R^1$ and $R^2$ is lower alkoxy, and the other is group of the formula: $-NHR^3$, in which $R^3$ is hydrogen, substituted or unsubstituted lower alkyl, substituted or unsubstituted lower alkoxy, substituted or unsubstituted amino, hydroxy or pyridylcarbonyl, or salts thereof, these compounds have excellent antithrombotic activity and are useful as antithrombotic drug, or synthetic intermediate for preparing other antithrombotic drug.

15 Claims, No Drawings

BUTADIENE DERIVATIVES AND PROCESS FOR USING THE SAME

This application is a divisional of application Ser. No. 08/033,804, filed on Mar. 18, 1993, U.S. Pat. No. 5,514,815 the entire contents of which are hereby incorporated by reference.

The present invention relates to novel butadiene derivatives which are useful as an antithrombotic drug or as an synthetic intermediate thereof, and further relates to processes for preparing the same.

PRIOR ART

It has been known that thrombus causes various diseases such as myocardial infarction, cerebral infarction, pulmonary infarction, and the like, and there have widely been used enzyme preparations such as tissue plasminogen activator, urokinase, streptokinase, and the like, for lysis and prevention of thrombus. These drugs have, however, some deficits, for example, they are rapidly inactivated in blood and as a result they lose their pharmacological activities, or they can be administered only by parenteral route but not by oral route.

On the other hand, there have been disclosed dibenzylidenesuccinic acid and N-methyl-dibenzylidenesuccinimide in Nouveau Journal De Chimie, Vol. 1, No. 5, 413–418 (1977), but their pharmacological activities have never been disclosed hitherto.

SUMMARY DESCRIPTION OF THE INVENTION

An object of the present invention is to provide novel butadiene derivatives having excellent antithrombotic activity which can be administered either orally or parenterally or are useful as a synthetic intermediate for antithrombotic drug. Another object of the present invention is to provide the processes for preparing the same.

DETAILED DESCRIPTION OF THE INVENTION

The desired butadiene derivatives of the present invention have the following formula [I].

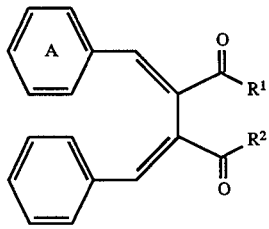

[I]

wherein Ring A is a tri-lower alkoxyphenyl group, $R^1$ and $R^2$ combine each other to form a group of the formula:

or one of $R^1$ and $R^2$ is a lower alkoxy group, and the other is a group of the formula: -$NHR^3$, in which $R^3$ is hydrogen atom, a substituted or unsubstituted lower alkyl group, a substituted or unsubstituted lower alkoxy group, a substituted or unsubstituted amino group, hydroxy group or pyridylcarbonyl group.

Suitable examples of the desired compounds [I] of the present invention are compounds of the formula [I], wherein Ring A is a tri-lower alkoxyphenyl group such as 3,4,5-tri-lower alkoxyphenyl group, 2,3,4-tri-lower alkoxyphenyl group, 2,4,5-tri-lower alkoxyphenyl group, 2,4,6-tri-lower alkoxyphenyl group, and the like, and $R^3$ is 1) hydrogen atom, 2) a lower alkyl group which may optionally be substituted by 1 to 3 groups selected from hydroxy group, a lower alkoxy group, carboxyl group, a lower alkoxycarbonyl group, an aralkyloxycarbonyl group (e.g. a phenyl-lower alkoxycarbonyl group, etc.), a di-lower alkylamino group, phenyl group and a nitrogen-containing 6-membered heterocyclic group (e.g. pyridyl group, morpholino group, etc.), 3) a lower alkoxy group which may optionally be substituted by a group selected from a lower alkoxy group and phenyl group, 4) an amino group which may optionally be substituted by a lower alkyl group, 5) hydroxy group, or 6) pyridylcarbonyl group.

The desired compounds [I] of the present invention have four stereoisomers owing to two double bonds thereof, and the present invention also includes these isomers and a mixture thereof.

In the desired compounds [I] of the present invention, the "lower alkyl group" and "lower alkoxy group" mean ones having 1 to 6 carbon atoms, preferably 1 to 4 carbon atoms, respectively, and the "aralkyl group" means phenyl-substituted lower alkyl groups having 7 to 8 carbon atoms.

The preferable compounds [I] as a medicine are, for example, compounds of the formula [I] wherein both two double bonds have E-configuration, Ring A is a 3,4,5-tri-lower alkoxyphenyl group, and $R^1$ and $R^2$ combine each other to form a group of the formula:

wherein $R^3$ is the same as defined above, among which the compounds of the formula [I] wherein $R^3$ is hydrogen atom, a lower alkyl group, a lower alkoxy group, a hydroxy-lower alkyl group, a morpholino-lower alkyl group or a pyridylcarbonyl group are more preferable as a medicine. The other preferable compounds as a medicine are compounds of the formula [I] wherein one of $R^1$ and $R^2$ is a lower alkoxy group, and the other is an amino group or a hydroxyamino group.

The desired compounds [I] of the present invention can be used either in the free form or in the form of a pharmaceutically acceptable salt thereof in clinical use.

The pharmaceutically acceptable salt includes, for example, alkali metal salts (e.g. sodium salt, potassium salt, etc.), alkaline earth metal salts (e.g. calcium salt, magnesium salt, etc.), inorganic acid addition salts (e.g. hydrochloride, hydrobromide, sulfate, etc.) and organic acid addition salts (e.g. maleate, oxalate, etc.).

The desired compounds [I] of the present invention and a pharmaceutically acceptable salt thereof can be administered in clinical use either orally or parenterally, and administered in the form of a pharmaceutical composition mixed with a pharmaceutical excipient suitable for oral administration or parenteral administration. The pharmaceutical compositions are, for example, solid preparations such as tablets, capsules, powders, and the like, or liquid preparations such as solutions, suspensions, emulsions, and the like. Moreover, when the desired compounds [I] of the present invention are administered parenterally, they may be used in the form of injection preparations, dermatologic preparations, suppositories, and the like.

The dosage of the compounds [I] may vary depending on age, weight, conditions of the patients, or severity of diseases to be cured, but it is usually in the range of 0.1 to 100 mg/kg/day, preferably 0.5 to 50 mg/kg/day in the case of oral administration. In the case of parenteral administration, it is in the range of 0.01 to 10 mg/kg/day, preferably 0.05 to 5 mg/kg/day.

According to the present invention, the desired 3-butenoic acid-type compounds [I] wherein one of $R^1$ and $R^2$ is a lower alkoxy group and the other is a group of the formula:-$NHR^3$, that is, the compounds of the formula [I-a]:

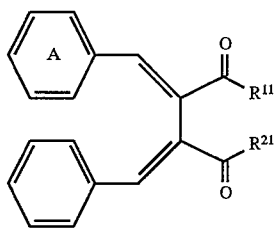
[I-a]

wherein one of $R^{11}$ and $R^{21}$ is a lower alkoxy group and the other is a group of the formula:-$NHR^3$, and Ring A and $R^3$ are the same as defined above, can be prepared, for example, by subjecting a compound of the formula [II]:

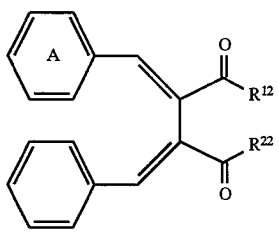
[II]

wherein one of $R^{12}$ and $R^{22}$ is a lower alkoxy group, and the other is hydroxy group, and Ring A is the same as defined above, or a salt, or a reactive derivative thereof, to condensation reaction with an amine compound of the formula [III]:

$NH_2R^3$ [III]

wherein $R^3$ is the same as defined above.

Moreover, the desired 2,5-pyrrolidinedione-type compounds [I] wherein $R^1$ and $R^2$ combine each other to form a group of the formula:

wherein $R^3$ is the same as defined above, that is, the compounds of the formula [I-A]:

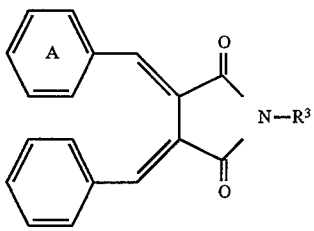
[I-A]

wherein Ring A and $R^3$ are the same as defined above, can be prepared, for example, by subjecting the compound [I-a] to internal cyclization reaction.

The desired N-substituted 2,5-pyrrolidinedione-type compounds [I], that is, the compounds of the formula [I-C]:

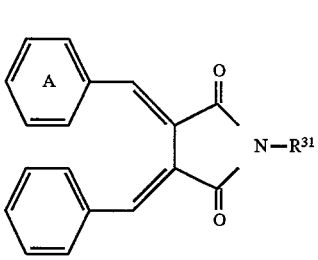
[I-C]

wherein $R^{31}$ is a substituted or unsubstituted lower alkyl group, a substituted or unsubstituted lower alkoxy group, a substituted or unsubstituted amino group or pyridylcarbonyl group, and Ring A is the same as defined above, can be prepared, for example, by subjecting an N-unsubstituted 2,5-pyrrolidinedione-type compound [I], that is, a compound of the formula [I-B]:

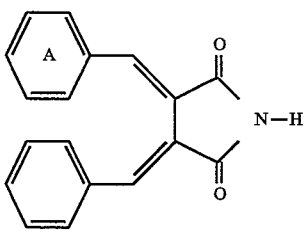
[I-B]

wherein Ring A is the same as defined above, to condensation reaction with a compound of the formula [IV]:

$X^1-R^{31}$ [IV]

wherein $X^1$ is a reactive residue, and $R^{31}$ is the same as defined above.

The 2,5-pyrrolidinedione-type compounds [I] wherein $R^3$ is a substituted or unsubstituted lower alkoxy group, that is, the compound of the formula [I-D]:

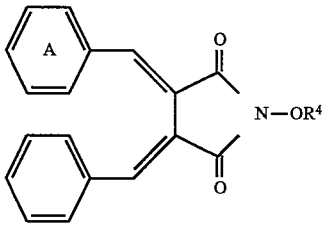
[I-D]

wherein $R^4$ is a substituted or unsubstituted lower alkyl group, and Ring A is the same as defined above, can be prepared by subjecting a compound [I] wherein one of $R^1$ and $R^2$ is a lower alkoxy group, and the other is a group of the formula: -NHOH, that is, a compound of the formula [I-b]:

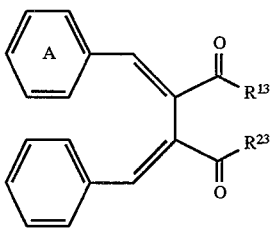
[I-b]

wherein one of $R^{13}$ and $R^{23}$ is a lower alkoxy group, and the other is a group of the formula: -NHOH, and Ring A is the same as defined above, to condensation reaction and internal cyclization reaction with a compound of the formula [V]:

$X^2-R^4$ [V]

wherein $X^2$ is a reactive residue, and $R^4$ is the same as defined above.

Among the compounds [I] obtained above, the 2,5-pyrrolidinedione-type compounds [I] can be converted from one derivative to other derivative, if necessary.

For example, the compounds [I] wherein $R^3$ is a carboxyl-substituted lower alkyl group, i.e. the compounds of the formula [I-E]:

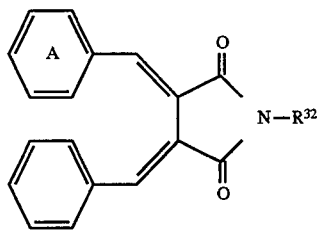

wherein $R^{32}$ is a carboxyl-substituted lower alkyl group, and Ring A is the same as defined above, can be prepared by treating a compound of the formula [I-F]:

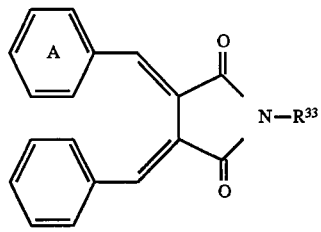

wherein $R^{33}$ is a lower alkoxycarbonyl-substituted lower alkyl group, and Ring A is the same as defined above, with an acid.

In the above process of the present invention, the condensation reaction between the butenoic acid ester-type compound [II] or a salt thereof with the amine compound [III] can be carried out in the presence of dehydrating agent in a suitable solvent. The dehydrating agent includes, for example, dicyclohexylcarbodiimide, carbonyldiimidazole, and the like. The salt of the butenoic acid ester [II] may be any conventional ones such as alkali metal salts, alkaline earth metal salts, and the like, and these salts may preferably be converted in advance into a free carboxylic acid and then used in the reaction with the amine compound [III].

The condensation reaction between a reactive derivative of the compound [II] and the amine compound [III] can be carried out in the presence or absence of an acid acceptor in a suitable solvent. The reactive derivative may be any conventional ones which are suitable for the acid-amide condensation reaction, for example, acid halides, mixed acid anhydrides, active esters, and the like. The acid acceptor includes, for example, alkali metal hydroxides, alkali metal carbonates, alkali metal hydrogen carbonates, trialkylamines, N,N-dialkylanilines, pyridine, and the like.

The suitable solvent may be any inert solvent which does not disadvantageously affect the reaction, for example, ethers (e.g. tetrahydrofuran, dioxane, etc.), trichloromethane, dichloromethane, and the like.

The condensation reaction can preferably be carried out at a temperature from under cooling to a boiling point of the solvent to be used, for example, at −20° C. to 100° C., more preferably at −10° C. to 70° C.

The 3-butenoic acid-type compounds [I-a] thus obtained can be used not only as a medicine but also as a synthetic intermediate for the 2,5-pyrrolidinedione-type compounds [I] having excellent antithrombotic activity.

The internal cyclization reaction of the 3-butenoic acid-type compounds [I-a] can be carried out in the presence of a base in a suitable solvent.

The base includes, for example, alkali metals (e.g. sodium, etc.), alkali metal hydroxides (e.g. sodium hydroxide, etc.), alkali metal hydrides (e.g. sodium hydride, etc.), alkali metal alcoholates (e.g. sodium methylate, etc.), lower alkyl-substituted alkali metal amides (e.g. lithium diisopropylamide, etc.), lower alkyl alkali metals (e.g. n-butyllithium, etc.), organic amines (e.g. tri-lower alkylamines, 1,8-diazabicyclo[5.4.0]undec-7-ene, etc.).

The solvent may be any inert solvent which does not disadvantageously affect the reaction, for example, organic solvents such as ethers (e.g. tetrahydrofuran, dioxane, etc.), alcohols (e.g. methanol, ethanol, etc.), dimethylformamide, and the like, or a mixture of water and these organic solvents.

The internal cyclization reaction of the compounds [I-a] can be carried out under cooling or with heating, for example, at −60° C. to 150° C., more preferably at a temperature from room temperature to a boiling point of the solvent to be used.

The condensation reaction between the N-unsubstituted pyrrolidinedione-type compound [I-B] and the compound [IV] can be carried out in the presence of an acid acceptor in a suitable solvent.

The reactive residue represented by $X^1$ is preferably a halogen atom.

The acid acceptor may be any conventional ones which are suitable in this kind of the reaction, for example, alkali metal hydrides (e.g. sodium hydride, etc.), alkali metal hydroxides (e.g. sodium hydroxide, etc.), alkali metal carbonates (e.g. potassium carbonate, etc.), alkali metal alcoholates (e.g. sodium methylate, etc.), lower alkyl-substituted alkali metal amides (e.g. lithium diisopropylamide, etc.) and alkali metals (e.g. sodium, etc.).

The solvent may be any inert solvent which does not disadvantageously affect the reaction, for example, ethers (e.g. tetrahydrofuran, etc.), dimethylformamide, dimethylsulfoxide, and the like.

The condensation reaction can be carried out at a temperature from under cooling to a boiling point of the solvent to be used, for example, at −60° C. to 100° C., more preferably at −60° to 20° C.

The condensation reaction and the internal cyclization reaction between the 3-butenoic acid-type compound [I-b] and the compound [V] can be carried out in the presence of a base in a suitable solvent.

The reactive residue represented by $X^2$ is preferably a halogen atom.

The base includes, for example, alkali metal hydroxides (e.g. sodium hydroxide, etc.), alkali metal hydrides (e.g. sodium hydride, etc.), alkali metal alcoholates (e.g. sodium methylate, etc.), lower alkyl-substituted alkali metal amides (e.g. lithium diisopropylamide, etc.) and alkali metals (e.g. sodium, etc.), and the like.

The solvent may be any inert solvent which does not disadvantageously affect the reaction, for example, ethers (e.g. tetrahydrofuran, etc.), dimethylformamide, dimethylsulfoxide, and the like.

These condensation reaction and cyclization reaction can be carried out at a temperature from under cooling to a boiling point of the solvent to be used, for example, at −60° C. to 5 100° C., more preferably at −60° C. to 20° C.

The acid treatment of the compound [I-F] can be carried out in a suitable solvent by a conventional method.

The solvent includes, for example, ethyl acetate, dichloromethane, benzene, and the like, and the acid may be any one which is conventionally used in this type of the reaction, for example, hydrogen chloride, p-toluenesulfonic acid, trifluoro-acetic acid, hydrogen bromide in glacial acetic acid, and the like.

In the above reactions, when the desired compounds [I] are obtained in the form of a mixture of stereoisomers, if necessary, these isomers can be separated by a conventional method such as silica gel column chromatography.

The starting compounds [II] of the present invention are a novel compound, and can be prepared by 1) condensation reaction between benzaldehyde or a tri-lower alkoxybenzaldehyde and a succinic acid di-lower alkyl ester to give a 3-lower alkoxy -carbonyl-4-phenyl (or tri-lower alkoxyphenyl)-3-butenoic acid, 2) followed by conventional esterification of the product to give a corresponding lower alkyl ester thereof, 3) and further reacting the product with a tri-lower alkoxybenzaldehyde [or benzaldehyde, in the case that a tri-lower alkoxybenzaldehyde is used in process 1)].

The above condensation reactions 1) and 3) can be carried out in the presence of a base (e.g. alkali metal alcoholate, etc.) under cooling or with heating, for example, at a temperature from −20° C. to a boiling point of the solvent to be used, in a suitable solvent.

In the present specification and claims, the "lower alkyl group" and the "lower alkoxy group" mean ones having 1 to 6 carbon atoms, preferably 1 to 4 carbon atoms, respectively, and the "aralkyl group" means phenyl-substituted lower alkyl groups having 7 to 8 carbon atoms.

Throughout the present description and claims, the stereochemistries of the double bonds may be either cis-configuration (Z) or trans-configuration (E)in the structures of the compounds having double bonds (e.g. the compounds [I], the compounds [II], etc.), unless specified otherwise.

EXAMPLES

The present invention is illustrated in more detail by the following Examples and Reference Examples, but should not be construed to be limited thereto.

Example 1

(1) A solution of (E)-3-methoxycarbonyl-4-phenyl-3-butenoic acid methyl ester (23.1 g) and 3,4,5-trimethoxybenzaldehyde (19.4 g) in t-butyl alcohol (100 ml) is added dropwise with stirring into a solution of potassium t-butoxide (11.1 g) in t-butyl alcohol (100 ml) at room temperature, and the mixture is stirred for one hour. The reaction mixture is poured into cold water (200 ml), and the mixture is extracted with isopropyl ether. The pH value of the aqueous layer is adjusted to pH 2-3, and the aqueous layer is extracted with ethyl acetate. The ethyl acetate layer is washed, dried, and evaporated to remove the solvent. The resulting residue is crystallized from diethyl ether to give (E)-2-[(E)-3,4,5-trimethoxybenzylidene]-3-carboxy-4-phenyl-3-butenoic acid methyl ester (25.7 g) as pale yellow crystals.

Yield: 65%

M.p. 153°–154° C. (recrystallized from ethyl acetate/isopropyl ether)

(2) To a solution of the above product (25.7 g) in trichloromethane (50 ml) is added thionyl chloride (4.7 ml) dropwise under ice-cooling, and thereto is added a drop of dimethylformamide. The mixture is refluxed for 30 minutes, and cooled to a temperature below 25° C. The mixture is added dropwise to conc. aqueous ammonia (20 ml) with vigorously stirring, and the resulting mixture is stirred for 30 minutes. The organic layer is separated, washed, dried, and evaporated to remove the solvent. The resulting residue is crystallized from diethyl ether, and collected by filtration to give (E)-2-[(E)-3,4,5-trimethoxybenzylidene]-3-carbamoyl-4-phenyl-3-butenoic acid methyl ester (24.9 g) as pale yellow crystals.

Yield: 97%

M.p. 179°–180° C. (recrystallized from ethyl acetate)

(3) To a solution of the above product (24.9 g) in tetrahydrofuran (75 ml) is added 2N aqueous sodium hydroxide solution (15.6 ml), and the mixture is refluxed for one hour. The mixture is cooled to room temperature, and thereto is added 2N hydrochloric acid (15.6 ml). The mixture is concentrated under reduced pressure, and to the residue is added trichloromethane. The mixture is washed, dried, and evaporated to remove the solvent. The resulting residue is recrystallized from ethyl acetate to give 3-[(E)-benzylidene]-4-[(E)-3,4,5-trimethoxybenzylidene]-2,5-pyrrolidinedione (17.6 g) as yellow plate crystals.

Yield: 77%

M.p. 158°–159° C.

The mother liquor of the above recrystallization is purified by silica gel column chromatography to give 3-[(E)-benzylidene]-4-[(Z)-3,4,5-trimethoxybenzylidene]-2,5-pyrrolidinedione as orange crystals.

M.p. 193°–195° C. (recrystallized from ethyl acetate/n-hexane)

Example 2

(1) (Z)-3-Methoxycarbonyl-4-phenyl-3-butenoic acid methyl ester is treated in the same manners as in Example 1-(1) and 1-(2) to give (Z)-2-[(E)-3,4,5-trimethoxybenzylidene]-3-carbamoyl-4-phenyl-3-butenoic acid methyl ester as colorless crystals.

M.p. 144°–146° C. (recrystallized from ethyl acetate/n-hexane)

(2) The above product is treated in the same manner as in Example 1-(3) to give 3-[(Z)-benzylidene]-4-[(E)-3,4,5-trimethoxybenzylidene]-2,5-pyrrolidinedione as yellow crystals.

M.p. 176°–178° C. (recrystallized from ethyl acetate/n-hexane)

Example 3

(1) (E)-3-Methoxycarbonyl-4-phenyl-3-butenoic acid methyl ester and 2,4,6-trimethoxybenzaldehyde are treated in the same manner as in Example 1-(1) to give (E)-2-[(E)-2,4,6-trimethoxybenzylidene]-3-carboxy-4-phenyl-3-butenoic acid methyl ester (foam) and (E)-2-[(Z)-2,4,6-trimethoxybenzylidene]-3-carboxy-4-phenyl-3-butenoic acid methyl ester (m.p. 208°–210° C.).

(2) (E)-2-[(E)-2,4,6-Trimethoxybenzylidene]-3-carboxy-4-phenyl-3-butenoic acid methyl ester is treated in the same manner as in Example 1-(2) to give (E)-2-[(E)-2,4,6-trimethoxybenzylidene]-3-carbamoyl-4-phenyl-3-butenoic acid methyl ester.

M.p. 173°–174° C.

Further, (E)-2-[(Z)-2,4,6-trimethoxybenzylidene]-3-carboxy-4-phenyl-3-butenoic acid methyl ester is treated in the same manner as in Example 1-(2) to give (E)-2-[(Z)-2,4,6-trimethoxybenzylidene]-3-carbamoyl-4-phenyl-3-butenoic acid methyl ester.

M.p. 169°–171° C. (recrystallized from ethyl acetate/n-hexane)

(3) (E)-2-[(E)-2,4,6-Trimethoxybenzylidene]-3-carbamoyl-4-phenyl-3-butenoic acid methyl ester is treated in the same manner as in Example 1-(3) to give 3-[(E)-benzylidene]-4-[(E)-2,4,6-trimethoxybenzylidene]-2,5-pyrrolidinedione.

M.p. 246°–248° C.

Example 4

(1) (E)-3-Methoxycarbonyl-4-(3,4,5-trimethoxyphenyl)-3-butenoic acid methyl ester and benzaldehyde are treated in the same manner as in Example 1-(1) to give (E)-2-[(E)-benzylidene]-3-carboxy-4-(3,4,5-trimethoxyphenyl)-3-butenoic acid methyl ester.

M.p. 131°–133° C.

(2) The above product is treated in the same manner as in Example 1-(2) to give (E)-2-[(E)-benzylidene]-3-carbamoyl-4-(3,4,5-trimethoxyphenyl)-3-butenoic acid methyl ester.

M.p. 121°–122° C.

(3) The above product is treated in the same manner as in Example 1-(3) to give 3-[(E)-benzylidene]-4-[(E)-3,4,5-trimethoxybenzylidene]-2,5-pyrrolidinedione.

Examples 5–8

(1) The corresponding starting compounds obtained in Reference Examples 1 and 4–5 are treated with a corresponding benzaldehyde derivative in the same manner as in Example 1-(1) to give the compounds of Table 1. The stereochemistries of the double bonds are both E-configuration.

TABLE 1

| Ex. No. | Ring A | $R^{22}$ | $R^{12}$ | Physical properties |
|---|---|---|---|---|
| 5-(1) | 3,4,5-tri(CH₃O)-phenyl | —OH | —OCH₂CH₃ | M.p. 137–138° C. |
| 6-(1) | 3,4,5-tri(CH₃O)-phenyl | —OH | —OCH(CH₃)₂ | Foam |
| 7-(1) | 2,3,4-tri(CH₃O)-phenyl | —OH | —OCH₃ | M.p. 93–94° C. |
| 8-(1) | 2,4,5-tri(CH₃O)-phenyl | —OH | —OCH₃ | M.p. 157–159° C. |

(2) The above products are treated in the same manner as in Example 1-(2) to give the compounds of Table 2. The stereochemistries of the double bonds are both E-configuration.

TABLE 2

[Structure: Ring A-CH=C(E)(COR¹)-CH(-)-C(E)(COR²)=CH-phenyl]

| Ex. No. | Ring A | R² | R¹ | Physical properties |
|---------|--------|-----|-----|---------------------|
| 5-(2) | 3,4,5-tri(CH₃O)-phenyl | —NH₂ | —OCH₂CH₃ | M.p. 129–130° C. |
| 6-(2) | 3,4,5-tri(CH₃O)-phenyl | —NH₂ | —OCH(CH₃)₂ | M.p. 131–132° C. |
| 7-(2) | 2,3,4-tri(CH₃O)-phenyl | —NH₂ | —OCH₃ | M.p. 141–142° C. |
| 8-(2) | 2,4,5-tri(CH₃O)-phenyl | —NH₂ | —OCH₃ | M.p. 200–201° C. |

(3) The above products are treated in the same manner as in Example 1-(3) to give the compounds of Table 3. The stereochemistries of the double bonds are both E-configuration.

TABLE 3

![Structure: Ring A-CH=C(C(=O))-C(C(=O))=CH-phenyl, with N-H bridging the two carbonyls, both double bonds E]

| Ex. No. | Ring A | Physical properties |
|---|---|---|
| 5-(3) | 3,4,5-tri(CH₃O)-phenyl | The same product as Example 1-(3) |
| 6-(3) | 3,4,5-tri(CH₃O)-phenyl | The same product as Example 1-(3) |
| 7-(3) | 2,3,6-tri(CH₃O)-phenyl | M.p. 183–184° C. |
| 8-(3) | 2,4-di(CH₃O), 5-OCH₃ phenyl | M.p. 224–225° C. |

Example 9

(1) To a solution of the compound (6.0 g) obtained in Example 1-(1) in trichloromethane (30 ml) is added dropwise thionyl chloride (1.1 ml) under ice-cooling, and thereto is added two drops of dimethylformamide. The mixture is refluxed for 30 minutes, and cooled to a temperature below 25° C. The mixture is added dropwise into 40% aqueous methylamine solution (10 ml) with vigorously stirring. The mixture is stirred for 30 minutes as it is, and the organic layer is separated, washed, dried, and evaporated to remove the solvent. The resulting residue is purified by silica gel column chromatography (solvent; trichloromethane :acetone=5:1) to give (E)-2-[(E)-3,4,5-trimethoxybenzylidene]-3-methylcarbamoyl-4-phenyl-3-butenoic acid methyl ester (5.4 g) as crystals.

Yield: 87%

M.p. 155°–157° C. (recrystallized from ethyl acetate/n-hexane)

(2) To a solution of the above product (3.5 g) in tetrahydrofuran (50 ml) is added 2N aqueous sodium hydroxide solution (2 ml), and the mixture is refluxed for one hour. The reaction solution is cooled to room temperature, and thereto is added 2N hydrochloric acid (2 ml). The mixture is concentrated under reduced pressure, and to the residue is added ethyl acetate. The mixture is washed, dried, and evaporated to remove the solvent, and the resulting residue is crystallized from diethyl ether to give (3E,4E)-1-methyl-3-benzylidene-4-(3,4,5-trimethoxybenzylidene)-2,5-pyrrolidinedione (2.8 g).

Yield: 87%

M.p. 131°–133° C. (recrystallized from ethyl acetate/isopropyl ether)

Examples 10–25

The corresponding starting compounds are treated in the same manner as in Example 9-(1) to give the compounds of Table 4. The stereochemistries of the double bonds are both E-configuration.

TABLE 4

![Structure: 3,4,5-trimethoxybenzylidene with E-COOCH₃ and phenyl with E-CONHR³]

| Ex. No. | R³ | Physical properties |
|---|---|---|
| 10 | —CH₂CH₂CH₂CH₃ | M.p. 86–88° C. |
| 11 | —CH(CH₃)₂ | Foam |
| 12 | —CH₂-phenyl | M.p. 130—132° C. |
| 13 | —CH₂CH₂OH | M.p. 110–111° C. |
| 14 | —C(CH₃)(CH₂OH)₂ | M.p. 116–117° C. |
| 15 | —C(CH₂OH)₃ | M.p. 130–131° C. |
| 16 | —CH(CH₂OH)₂ | Foam |
| 17 | —CH₂CH₂OCH₃ | M.p. 88–90° C. |
| 18 | —OH | M.p. 193° C. (decomposed) |
| 19 | —OCH₃ | M.p. 163–164° C. |
| 20 | —NH₂ | M.p. 175–176° C. |
| 21 | —N(CH₃)₂ | M.p. 124–126° C. |
| 22 | —CH₂-(4-pyridyl) | |
| 23 | —CH₂-(3-pyridyl) | M.p. 108–110° C. |
| 24 | —CH₂CH₂N(morpholino) | M.p. 143–144° C. |
| 25 | —OCH₂-phenyl | Oil |

Examples 26–38

The corresponding starting compounds are treated in the same manner as in Example 9-(2) to give the compounds of Table 5. The stereochemistries of the double bonds are both E-configuration.

TABLE 5

[Structure: 3,4,5-trimethoxybenzylidene and benzylidene substituents on a pyrrolidinedione ring with N—R³, both double bonds labeled E]

| Ex. No. | R³ | Salt | Physical properties |
|---|---|---|---|
| 26 | —CH₂—(phenyl) | Free | M.p. 132–134° C. |
| 27 | —CH₂CH₂OH | Free | M.p. 103–105° C. |
| 28 | —C(CH₃)(CH₂OH)₂ | Free | M.p. 125–126° C. |
| 29 | —C(CH₂OH)₃ | Free | M.p. 161–162° C. |
| 30 | —CH(CH₂OH)₂ | Free | Foam |
| 31 | —CH₂CH₂OCH₃ | Free | M.p. 148–149° C. |
| 32 | —OCH₃ | Free | M.p. 131–133° C. |
| 33 | —NH₂ | Hydrochloride | M.p. 108° C. (decomposed) |
| 34 | —N(CH₃)₂ | Free | M.p. 159–161° C. |
| 35 | —CH₂-(2-pyridyl) | Hydrochloride | M.p. 204° C. (decomposed) |
| 36 | —CH₂-(3-pyridyl) | Hydrochloride | M.p. 203° C. (decomposed) |
| 37 | —CH₂CH₂N(morpholino) | Hydrochloride | M.p. 195° C. |
| 38 | —OCH₂-(phenyl) | Free | M.p. 137–138° C. |

Example 39

To a suspension of 62% sodium hydride (0.33 g) in dimethylformamide (10 ml) is added dropwise a solution of (E)-2-(E)-3,4,5-trimethoxybenzylidene]-3-hydroxycarbamoyl-4-phenyl -3-butenoic acid methyl ester (3.8 g) in dimethylformamide (10 ml) under ice-cooling, and the mixture is stirred at room temperature for two hours. To the mixture is added dropwise methoxymethyl chloride (0.67 ml) under ice-cooling, and the mixture is stirred at room temperature for two days, and then evaporated to remove the solvent. To the residue is added ethyl acetate, and the mixture is washed, dried, and evaporated to remove the solvent. The resulting residue is purified by silica gel column chromatography (solvent; n-hexane:trichloromethane:ethyl acetate=5:5:4) to give (3E, 4E)-1-methoxymethoxy-3 -benzylidene-4-(3,4,5-trimethoxybenzylidene)-2,5-pyrrolidinedione (1.25 g) as yellow crystals.

Yield: 37%

M.p. 175°–177° C. (recrystallized from ethyl acetate/n-hexane)

Example 40

To a suspension of 63.2% sodium hydride (0.38 g) in dimethylformamide (10 ml) is added dropwise a solution of (3E, 4E)-3-benzylidene-4-(3,4,5-trimethoxybenzylidene)-2,5-pyrrolidinedione (3.65 g) in dimethylformamide (10 ml) under ice-cooling, and the mixture is stirred at room temperature for one hour. To the mixture is added dropwise methoxymethyl chloride (0.84 ml) under ice-cooling, and the mixture is stirred at room temperature overnight. The mixture is evaporated to remove the solvent, and to the residue is added ethyl acetate. The mixture is washed, dried, and evaporated to remove the solvent. The resulting residue is purified by silica gel column chromatography (solvent; n-hexane:trichloromethane:ethyl acetate=5:5:4) to give (3E, 4E)-1-methoxymethyl-3-benzylidene-4-(3,4,5-trimethoxybenzylidene)-2,5-pyrrolidinedione (3.0 g) as yellow crystals.

Yield: 73%

M.p. 127°–128° C. (recrystallized from ethyl acetate/n-hexane)

Examples 41–45

The corresponding starting compounds are treated in the same manner as in Example 40 to give the compounds of Table 6. The stereochemistries of the double bonds are both E-configuration.

TABLE 6

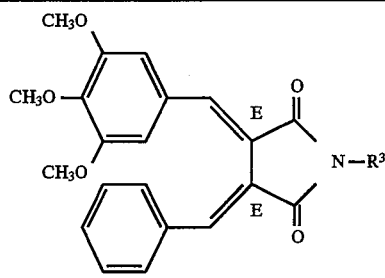

| Ex. No. | R³ | Salt | Physical properties |
|---|---|---|---|
| 41 | —CH₂CH₂N(CH₃)₂ | Hydrochloride | M.p. 202° C. (decomposed) |
| 42 | —CH₂COOC(CH₃)₃ | Free | Foam |
| 43 | —CO—⟨pyridyl⟩ | Hydrochloride | M.p. 200° C. (decomposed) |
| 44 | —CO—⟨pyridyl⟩ | Hydrochloride | M.p. 196° C. (decomposed) |
| 45 | —CH₂COOCH₂—⟨phenyl⟩ | Free | M.p. 127–129° C. |

Example 46

(1) To a solution of (3E,4E)-1-t-butoxycarbonylmethyl-3-benzylidene-4-(3,4,5-trimethoxybenzylidene)-2,5-pyrrolidinedione (3.5 g) obtained in Example 42 in dichloromethane (40 ml) is added trifluoroacetic acid (10 ml) at room temperature, and the mixture is allowed to stand for 4 hours. The mixture is evaporated under reduced pressure to remove the solvent, and to the residue is added trichloromethane. The mixture is washed, dried, and evaporated to remove the solvent. The resulting residue is crystallized from diethyl ether to give (3 E,4E)- 1 -carboxymethyl-3-benzylidene-4-(3,4,5-trimethoxybenzylidene) -2,5-pyrrolidinedione (2.5 g) as yellow prisms.

Yield: 81%

M.p. 183°–185° C.

(2) The above product (2.38 g) is dissolved in a mixture of tetrahydrofuran (10 ml) and methanol (10 ml), and thereto is added 2N aqueous sodium hydroxide solution (2.8 ml). The mixture is evaporated to remove the solvent, and to the residue is added trichloromethane. The mixture is dried and evaporated to remove the solvent, and the resulting crystalline residue is recrystallized from a mixture of ethyl acetate and diethyl ether to give (3E,4E)-1-carboxymethyl-3-benzylidene-4-(3,4,5-trimethoxybenzylidene)-2,5-pyrrolidinedione sodium salt (2.3 g) as yellow crystals.

Yield: 74%

M.p. 190° C. (decomposed)

Reference Example 1

To a solution of potassium t-butoxide (16.8 g) in t-butyl alcohol (150 ml) is added dropwise with stirring a solution of benzaldehyde (15.9 g) and succinic acid dimethyl ester (26.3 g) in t-butyl alcohol (20 ml) at room temperature, and the mixture is stirred for 30 minutes. The reaction mixture is poured into ice-water (200 ml), and the mixture is extracted with isopropyl ether. The pH value of the aqueous layer is adjusted to pH 2-3, and the mixture is extracted with ethyl acetate. The ethyl acetate layer is washed, dried, and evaporated to remove the solvent. The residue is dissolved in methanol (75 ml), and thereto is added dropwise thionyl chloride (10.9 ml) under ice-cooling. The mixture is allowed to stand at room temperature overnight, and then evaporated to remove the solvent. To the residue is added isopropyl ether, and the mixture is washed, dried, and evaporated to remove the solvent. The resulting residue is distilled under reduced pressure to give (E)-3-methoxycarbonyl-4-phenyl-3-butenoic acid methyl ester (23.2 g) as colorless oil.

Yield: 66%

B.p. 135°–137° C. (0.3 mmHg)

Reference Example 2

Benzaldehyde (21.2 g) and succinic acid dimethyl ester (40.9 g) are treated in the same manner as in Reference Example 1, and the resulting product is purified by silica gel column chromatography to give (Z)-3-methoxycarbonyl-4-phenyl-3-butenoic acid methyl ester (2.3 g) as colorless syrup.

Reference Example 3

3,4,5-Trimethoxybenzaldehyde and succinic acid dimethyl ester are treated in the same manner as in Reference Example 1 to give (E)-3-methoxycarbonyl-4-(3,4,5-trimethoxyphenyl) -3-butenoic acid methyl ester as pale yellow syrup.

Reference Examples 4–5

The corresponding starting compounds are treated in the same manner as in Reference Example 1 to give the compounds of Table 7. The stereochemistry of the double bond is E-configuration.

TABLE 7

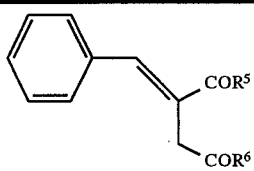

| Ref. Ex. No. | R⁶ | R⁵ | Physcial properties |
|---|---|---|---|
| 4 | —OCH$_2$CH$_3$ | —OCH$_2$CH3 | Pale yellow syrup |
| 5 | —OCH(CH$_3$)$_2$ | —OCH$_3$ | Pale yellow syrup |

Effects of the Invention

The desired butadiene derivatives [I] of the present invention and pharmaceutically acceptable salts thereof enhance fibrinolysis and show excellent antithrombotic activity by either oral administration or parenteral administration. Hence, they can be used as antithrombotic drug in the prophylaxis or treatment of various blood vessel diseases such as myocardial infarction, cerebral infarction, pulmonary infarction, deep venous thrombosis, peripheral arterial embolism, angina pectoris, dissminated intravascular coagulation containing septicemia and other venous embolism, and diabetic complications. Moreover, the butadiene derivatives [I] of the present invention and pharmaceutical acceptable salts thereof can also be used as preventive for re-occulusion of the blood vessel after a pecutaneous transluminal coronary angioplasty or thrombolytic therapy.

Among the desired butadiene derivatives [I] of the present invention, the 3-butenoic acid-type compounds per se have antithrombotic activity, but they can also be used as an intermediate for preparing the 2,5-pyrrolidinedione-type compounds having excellent antithrombotic activity.

What is claimed is:

1. A butadiene compound of the formula (I):

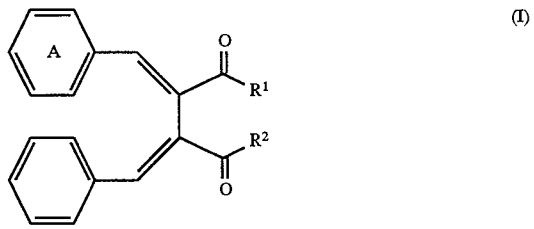

(I)

wherein,

Ring A is a tri-lower alkoxyphenyl group, one of R$^1$ and R$^2$ is a lower alkoxy group, and the other is a group of the formula: -NHR$^3$, in which R$^3$ is 1) a hydrogen atom, 2) a lower alkyl group which may optionally be substituted by 1 to 3 groups selected from a hydroxy group, a lower alkoxy group, carboxyl group, a lower alkoxycarbonyl group, a phenyl-lower alkoxycarbonyl group, a di-lower alkylamino group, a phenyl group, a pyridyl group and a morpholino group, 3) a lower alkoxy group which may optionally be substituted by a lower alkoxy group or a phenyl group, 4) an amino group which may optionally be substituted by a lower alkyl group, 5) a hydroxy group, or 6) a pyridylcarbonylgroup, or a pharmaceutically acceptable salt thereof.

2. The compound according to claim 1, wherein the double bonds both have an E-configuration.

3. The compound according to claim 1 or 2, wherein Ring A is a 3,4,5-tri-lower alkoxyphenyl group.

4. The compound according to claim 1 or 2, wherein R$^3$ is 1) a hydrogen atom, 2) a lower alkyl group which may optionally be substituted by 1 to 3 groups selected from a hydroxy group, a lower alkoxy group, a phenyl group, a pyridyl group and a morpholino group, 3) a lower alkoxy group which may optionally be substituted by a phenyl group, 4) an amino group which may be substituted by a lower alkyl group, 5) a hydroxy group, or 6) a pyridylcarbonyl group.

5. The compound according to claim 1 or 2, wherein R$^3$ is a hydrogen atom, a lower alkyl group, a lower alkoxy group, a hydroxy-lower alkyl group, a morpholino-lower alkyl group or a pyridylcarbonyl group.

6. The compound according to claim 1 or 2, wherein R$^3$ is a hydrogen atom.

7. (E)-2-[(E)-3,4,5-Trimethoxybenzylidene]-3-carbamoyl-4-phenyl-3-butenoic acid methyl ester or a pharmaceutically acceptable salt thereof.

8. A butenoic acid ester of the formula [II]:

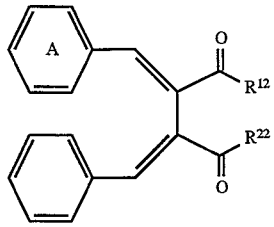

[II]

wherein Ring A is a tri-lower alkoxyphenyl group, and one of R$^{12}$ and R$^{22}$ is a lower alkoxy group, and the other is hydroxy group, or a salt thereof.

9. The compound according to claim 1, wherein, the configuration of the double bond attached to Ring A in Formula (I) is E or Z; the configuration of the other double bond attached to the benzene ring thereof is E; Ring A is substituted by three C$_{1-6}$ lower alkoxy groups; and one of R$^1$ and R$^2$ is a C$_{1-6}$ lower alkoxy group, and the other is a group of the formula

wherein,

R$^3$ is selected from the group consisting of:

a C$_{1-6}$ lower alkyl group, a hydroxy group, a C$_{1-6}$ lower alkoxy group, a phenyl-C$_{1-6}$ lower alkoxy group, an amino group, a di-(C$_{1-6}$ lower alkyl)-amino group and a C$_{1-6}$ lower alkyl group substituted by 1 to 3 substituents selected from the group consisting of a hydroxy group, a C$_{1-6}$ lower alkoxy group, a phenyl group, a 2-pyridyl group, a 4-pyridyl group and a morpholino group.

10. The compound according to claim 9, wherein both double bonds attached to Ring A and the benzene ring in Formula (I) have an E-configuration.

11. The compound according to claim 10, wherein Ring A is a 3,4,5-tri(C$_{1-6}$ lower alkoxy) phenyl group.

12. A pharmaceutical composition comprising an effective amount of a compound as set forth in claim 1 or 9 or a pharmaceutically acceptable salt thereof and a pharmaceutically acceptable carrier or diluent.

13. A method for the prophylaxis or treatment of blood vessel diseases and diabetic complications in a warm-blooded animal, which method comprises administering to said warm-blooded animal an effective amount of a compound as set forth in claim 1 or 9.

14. A method of producing an antithrombotic action in a warm blooded patient in need thereof, said method comprising:

administering to said patient an effective antithrombotic amount of said compound of Formula (I) or said pharmaceutically acceptable salt thereof as recited in claim 1 or 9.

15. The method as recited in claim 13, wherein said warm blooded animal has a medical condition selected from the group consisting of:

a myocardial infarction,
a cerebral infarction,
a pulmonary infarction,
a deep venous thrombosis,
a peripheral arterial embolism,
an angina pectoris,
a disseminated intravascular coagulation containing septicemia,
a venous embolism and
a diabetic complication.

* * * * *